US012109071B2

(12) United States Patent
Lee et al.

(10) Patent No.: US 12,109,071 B2
(45) Date of Patent: Oct. 8, 2024

(54) ULTRASONIC DIAGNOSTIC DEVICE PROVIDING USER PRESET AND METHOD FOR OPERATING SAME

(71) Applicant: SAMSUNG MEDISON CO., LTD., Hongcheon-gun Gangwon-do (KR)

(72) Inventors: Jaesung Lee, Seongnam-si (KR); Ara Cho, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 330 days.

(21) Appl. No.: 17/428,143

(22) PCT Filed: Feb. 5, 2020

(86) PCT No.: PCT/KR2020/001676
§ 371 (c)(1),
(2) Date: Aug. 3, 2021

(87) PCT Pub. No.: WO2020/162683
PCT Pub. Date: Aug. 13, 2020

(65) Prior Publication Data
US 2022/0125416 A1    Apr. 28, 2022

(30) Foreign Application Priority Data

Feb. 8, 2019 (KR) ........................ 10-2019-0015190

(51) Int. Cl.
*A61B 8/00* (2006.01)
*A61B 8/08* (2006.01)

(52) U.S. Cl.
CPC .............. *A61B 8/585* (2013.01); *A61B 8/465* (2013.01); *A61B 8/5292* (2013.01); *A61B 8/54* (2013.01)

(58) Field of Classification Search
None
See application file for complete search history.

(56) References Cited

U.S. PATENT DOCUMENTS

| 8,509,508 | B2 | 8/2013 | Choi et al. |
| 8,751,961 | B2 | 6/2014 | Bird et al. |
| 9,152,761 | B2 | 10/2015 | Bhatia et al. |
| 9,715,575 | B2 | 7/2017 | Cohen-Solal et al. |
| 10,706,506 | B2 | 7/2020 | Dhanantwari et al. |
| 11,020,090 | B2 | 6/2021 | Yoon et al. |

(Continued)

FOREIGN PATENT DOCUMENTS

| JP | 2009-077960 A | 4/2009 |
| JP | 2011-251120 A | 12/2011 |

(Continued)

OTHER PUBLICATIONS

Extended European Search Report dated Sep. 28, 2022 issued in European Patent Application No. 20752311.9.

(Continued)

*Primary Examiner* — Jonathan Cwern
(74) *Attorney, Agent, or Firm* — Morgan, Lewis & Bockius LLP

(57) ABSTRACT

An ultrasonic diagnostic device providing a user preset and a method of operating same. In one embodiment, an ultrasonic diagnostic device can display change history information and use history information of at least one user preset.

11 Claims, 15 Drawing Sheets

(56) References Cited

U.S. PATENT DOCUMENTS

| | | | |
|---|---|---|---|
| 2006/0241455 A1* | 10/2006 | Shvarts | G01S 7/5205 |
| | | | 600/447 |
| 2010/0010345 A1 | 1/2010 | Shin et al. | |
| 2013/0072781 A1* | 3/2013 | Omernick | G16H 40/40 |
| | | | 600/407 |
| 2013/0253317 A1 | 9/2013 | Gauthier | |
| 2014/0088428 A1* | 3/2014 | Yang | G06F 3/04847 |
| | | | 600/443 |
| 2017/0071570 A1* | 3/2017 | Jumatsu | A61B 8/4411 |

FOREIGN PATENT DOCUMENTS

| | | |
|---|---|---|
| JP | 2012-213620 A | 11/2012 |
| JP | 2013-154162 A | 8/2013 |
| JP | 2013-545577 A | 12/2013 |
| JP | 2014-193193 A | 10/2014 |
| JP | 6053749 B2 | 12/2016 |
| KR | 10-2010-0007819 A | 1/2010 |
| KR | 10-2016-0108978 A | 9/2016 |
| KR | 10-2016-0125484 A | 10/2016 |
| KR | 10-1718675 B1 | 3/2017 |
| WO | 2016/068604 A1 | 5/2016 |

OTHER PUBLICATIONS

International Search Report and Written Opinion dated May 12, 2020 issued in International Patent Application No. PCT/KR2020/001676 (with English translation).

Office Action issued Dec. 21, 2023 for Korean Patent Application No. 10-2019-0015190 (See English Translation).

* cited by examiner

FIG. 6B

| CHANGE HISTORY/<br>USE HISTORY GRAPH | | USER PRESET A | USER PRESET B | USER PRESET C | USER PRESET D |
|---|---|---|---|---|---|
| | | CHANGE / USE<br>HISTORY / HISTORY | CHANGE / USE<br>HISTORY / HISTORY | CHANGE / USE<br>HISTORY / HISTORY | CHANGE / USE<br>HISTORY / HISTORY |
| CHANGE HISTORY | PERIOD OF MODIFICATION | ONE YEAR AND TWO MONTHS AGO | ONE YEAR AND TWO MONTHS AGO | ONE DAY AGO | FIVE DAYS AGO |
| | NUMBER OF MODIFIED ITEMS | 18 | 17 | 182 | 162 |
| | NUMBER OF MODIFICATIONS | 8 | 9 | 308 | 288 |
| USE HISTORY | NUMBER OF USES | 4,560 | 40 | 45 | 4,060 |
| | PERIOD OF USE | ONE DAY AGO | ONE YEAR AND ONE MONTH AGO | ONE DAY AGO | ONE DAY AGO |
| | TIME OF USE | 21,562 MINUTES | 262 MINUTES | 302 MINUTES | 18,562 MINUTES |
| | NUMBER OF DIAGNOSED PATIENTS | 3,402 | 32 | 34 | 3,002 |
| OPTIMIZATION DEGREE | | COMPLETION STAGE | INITIAL STAGE | INITIAL STAGE | INTERMEDIATE STAGE |

600B

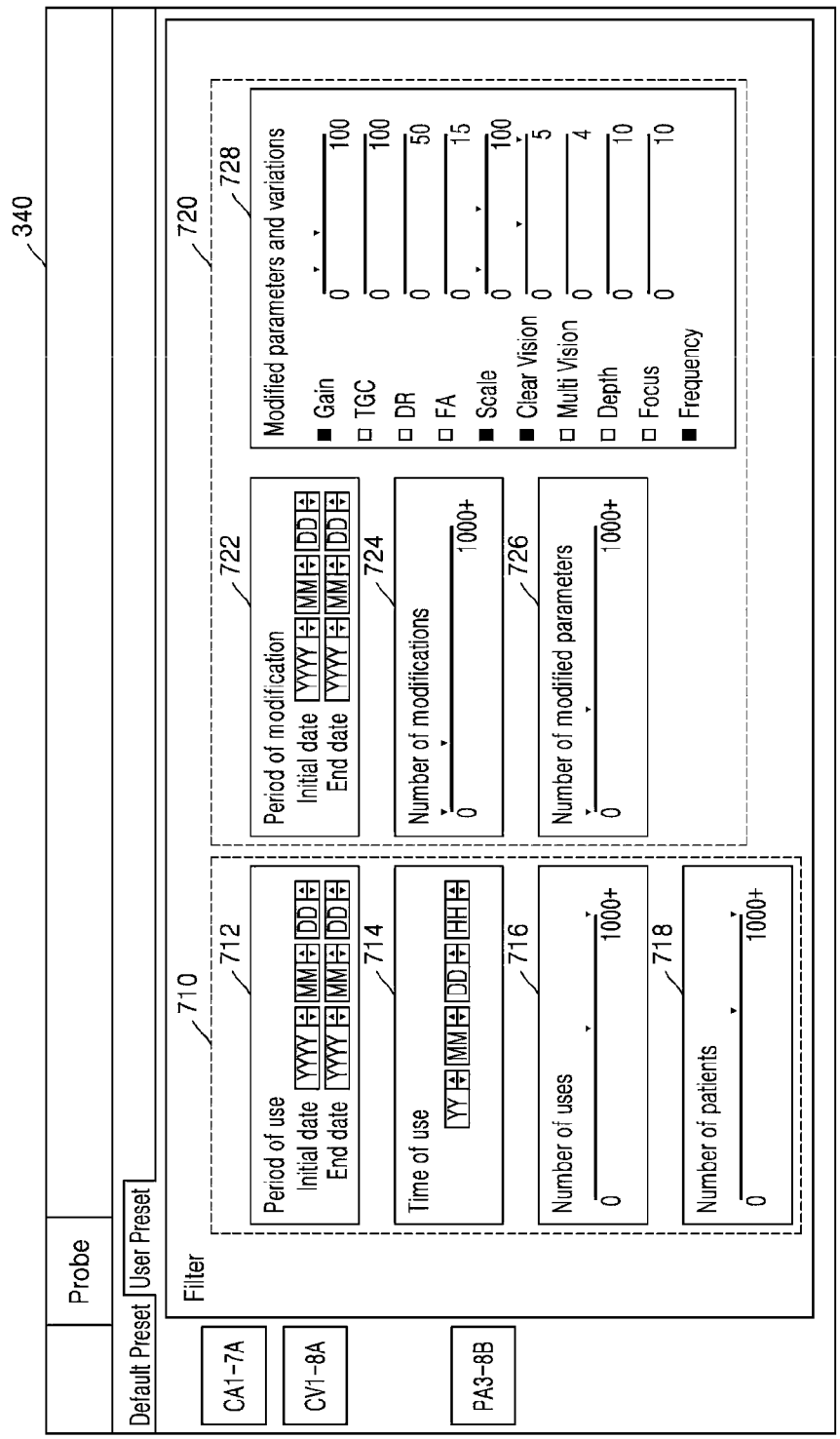

ULTRASONIC DIAGNOSTIC DEVICE PROVIDING USER PRESET AND METHOD FOR OPERATING SAME

CROSS-REFERENCE OF RELATED APPLICATIONS

This application is the U.S. National Phase under 35 U.S.C. § 371 of International Patent Application No. PCT/KR2020/001676, filed on Feb. 5, 2020, which in turn claims the benefit of Korean Application No. 10-2019-0015190, filed on Feb. 8, 2019, the entire disclosures of which applications are incorporated by reference herein.

TECHNICAL FIELD

The present disclosure relates to an ultrasonic diagnostic device providing a user preset and a method of operating same, and more particularly, to an apparatus and method for providing a user preset in which various set parameters of the ultrasonic diagnostic device used to obtain an ultrasound image of an object are optimized.

BACKGROUND

Ultrasonic diagnostic devices irradiate ultrasound signals generated by transducers of a probe to an object and receive information about signals reflected from the object, thereby obtaining at least one image of an internal part of the object (e.g., soft tissue or blood flow).

A user (e.g., a medical doctor, a nurse, a medical laboratory technologist, or a medical imaging expert), who examines an object using an ultrasonic diagnostic device, may modify items and values of various set parameters of the ultrasonic diagnostic device while obtaining an ultrasound image of the object and examining the object. The user does not use a factory preset, which is an initial setting value of the ultrasonic diagnostic device, but generates a user preset by modifying the set parameters while diagnosing, according to a patient, a part to be examined, a diagnosis division, or a user's personal preference, and storing the modified parameters. The user additionally captures ultrasound images of several patients in order to confirm whether the modified set parameter value of the user preset is appropriate. The user preset may be optimized through the process of capturing the ultrasound image multiple times.

In general, in order for a user preset to be optimized, it takes time and effort. In addition, it takes a lot of time for a user, who does not have knowledge or is not experienced in an ultrasonic diagnostic device, to generate a preferred user preset. Further, there is a problem in that, when an ultrasound image is captured using an unoptimized user preset, the ultrasound image with satisfactory quality may not be obtained.

DISCLOSURE

Technical Problem

The present disclosure provides an ultrasonic diagnostic device that provides a user preset with reliability in order to reduce the time and effort required in the process of optimizing the user preset, and a method of operating same.

Advantageous Effects

An ultrasonic diagnostic device of the present disclosure can reduce the time and effort required in the process of optimizing a user preset and, as a result, can improve user convenience. In addition, the ultrasonic diagnostic device of the present disclosure can improve the quality of an ultrasound image by providing highly reliable user presets used by others.

DESCRIPTION OF DRAWINGS

The present invention, can be easily understood from the following detailed description and combination of the accompanying drawings, in which reference numerals denote structural elements.

FIG. 6b is a table illustrating parameters representing the change history and the use history of the user preset.

FIG. 7 is a diagram illustrating an example of a user interface for receiving a user input, which is used for setting reference values related to change history information and use history information of a user preset, by the ultrasonic diagnostic device of the present disclosure.

TECHNICAL SOLUTION

Figure 1:
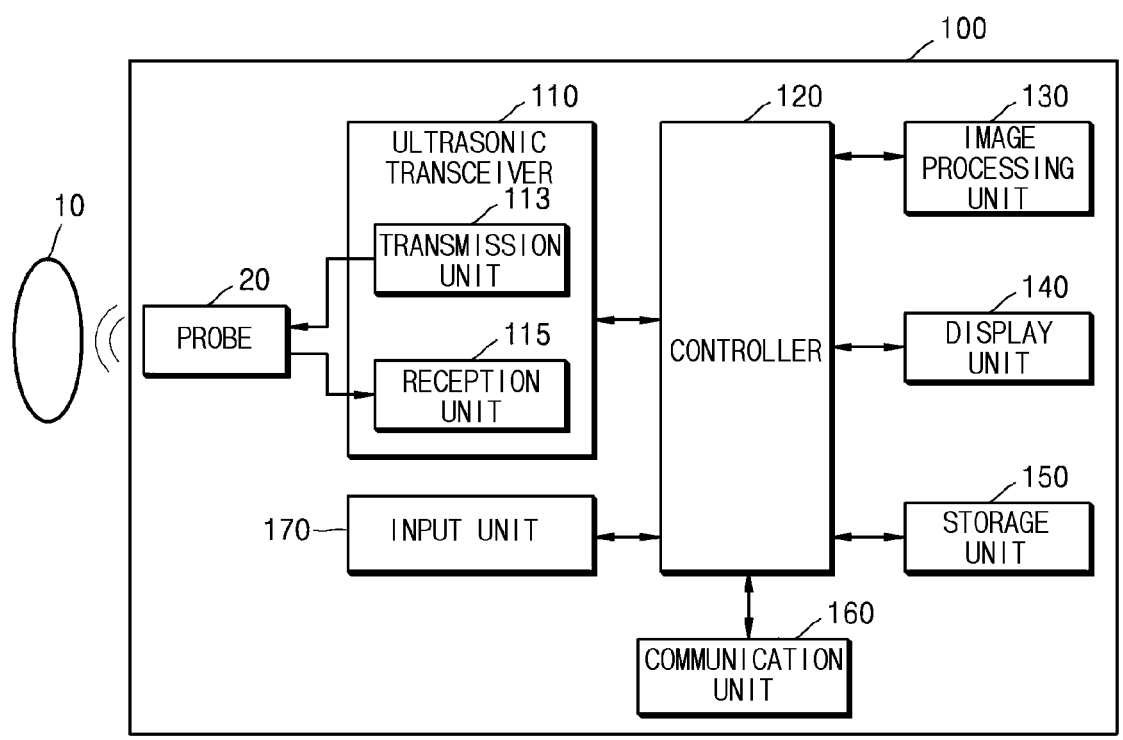
FIG. 1 is a block diagram illustrating a configuration of an ultrasonic diagnostic device.

As a technical means for solving the above-described technical problem, an embodiment of the present disclosure provides an ultrasonic diagnostic device including a display unit, a storage unit configured to store at least one user preset, a user input unit configured to receive a user input for modifying a set parameter of each of the at least one user preset, and a controller configured to store change history information of the at least one user preset, whose set parameter is modified based on the user input, in the storage unit, obtain use history information that is used by the at least one user preset in capturing an ultrasound image of an object, store the obtained use history information in the storage unit, and display the change history information and the use history information related to the at least one user preset on the display unit.

For example, the change history information may include information about at least one of a period of modification of the set parameter, the number of modifications, the number of modified items of the set parameter, and modified variations of the set parameter value of each of the at least one user preset.

For example, the user input unit may receive a user input for setting a reference value related to at least one of the period of modification of the set parameter, the number of modifications, the number of items of the set parameter, and the modified variations of the set parameter value, and the controller may set, based on the received user input, the reference value related to at least one of the period of modification of the set parameter, the number of modifications, the number of items of the set parameter, and the modified variations of the set parameter value and determine the user preset corresponding to the set reference value among the at least one user preset.

For example, the use history information may include information about at least one of a period of use, a time of use, the number of uses, and the number of diagnosed patients of each of the at least one user preset.

For example, the user input unit may receive a user input for setting a reference value related to at least one of the period of use, the time of use, the number of uses, and the number of diagnosed patients of each of the at least one user preset, and the controller may set, based on the received user input, the reference value related to at least one of the period of use, the time of use, the number of uses, and the number of diagnosed patients of each of the at least one user preset and determine the user preset corresponding to the set reference value among the at least one user preset.

For example, the controller may determine reliability of the at least one user preset based on the change history information and the use history information and display a first user preset having high reliability among the at least one user preset previously stored in the storage unit on the display unit.

For example, as a period of modification of the set parameter of the at least one user preset increases, the number of modifications of the set parameter of the at least one user preset decreases, the number of modified items of the set parameter decreases, and the modified variations of the set parameter value decrease, the controller may determine that the user preset is highly reliable among the at least one user preset.

For example, the controller may determine reliability of the at least one user preset in proportion to a time of use, the number of uses, and the number of diagnosed patients of the at least one user preset during a preset time period.

For example, the controller may quantify the change history information and the use history information of the at least one user preset and display the quantified change history information and use history information on the display unit in the form of a graph.

For example, the user input unit may receive a user input for selecting one probe, which is used for capturing the object, among a plurality of different probes, and the controller may set a diagnosis division that is diagnosed using the selected probe based on the received user input and display a second user preset having high reliability among the at least one user preset corresponding to the set diagnosis division.

As a technical means for solving the above-described technical problem, an embodiment of the present disclosure provides a method of operating an ultrasonic diagnostic device including steps of storing change history information of at least one user preset when a set parameter of the at least one user preset is modified, obtaining use history information used by the at least one user preset in capturing an ultrasound image of an object and storing the obtained use history information, and displaying the change history information and the use history information related to the at least one user preset.

For example, in the step of storing the change history information, at least one of a period of modification of the set parameter, the number of modifications, the number of modified items of the set parameter, and the modified variations of the set parameter value of each of the at least one user preset may be stored.

For example, a reference value related to at least one of the period of modification of the set parameter, the number of modifications, the number of modified items of the set parameter, and the modified variations of the set parameter value may be set based on a user input.

For example, the use history information may include information about at least one of a period of use, a time of use, the number of uses, and the number of diagnosed patients of each of the at least one user preset.

For example, a reference value related to at least one of the period of use, the time of use, the number of uses, and the number of diagnosed patients of each of the at least one user preset may be set based on a user input.

For example, the method may further include steps of determining reliability of the at least one user preset based on the change history information and the use history information, and displaying a first user preset having high reliability among the at least one user preset previously stored in the ultrasonic diagnostic device.

For example, in the step of determining the reliability of the at least one user preset, as a period of modification of the set parameter of the at least one user preset increases, the number of modifications of the set parameter of the at least one user preset decreases, the number of modified items of the set parameter decreases, and modified variations of the set parameter value decrease, the user preset may be determined as being highly reliable among the at least one user preset.

For example, in the step of determining the reliability of the at least one user preset, the reliability of the at least one user preset may be determined in proportion to a time of use, the number of uses, and the number of diagnosed patients of the at least one user preset during a preset time period.

For example, the method may further include steps of selecting one probe, which is used for capturing the object, among a plurality of different probes based on a user input, and setting a diagnosis division that is diagnosed using the selected probe, wherein in the step of displaying the at least one user preset, a second user preset having high reliability may be displayed among the user presets corresponding to the set diagnosis division.

As a technical means for solving the above-described technical problem, an embodiment of the present disclosure provides a computer program product including a computer-readable storage medium, wherein the storage medium may include instructions for performing steps of storing change history information of at least one user preset in a storage unit in an ultrasonic diagnostic device when a set parameter of the at least one user preset is modified, obtaining use history information used by the at least one user preset in capturing an ultrasound image of an object and storing the obtained use history information, and displaying both the change history information and the use history information related to the at least one user preset.

DETAILED DESCRIPTION

The present specification describes the principles of the present invention and discloses embodiments such that the scope of the present invention may be clarified and those skilled in the art to which the present invention pertains may implement the present invention. The disclosed embodiments may be implemented in various forms.

A reference numeral attached in each of operations is used to identify each of the operations, and this reference numeral does not describe the order of the operations, and the operations may be performed differently from the described order unless clearly specified in the context. The term 'module' or 'unit' used in this specification may be implemented as one or a combination of two or more of software, hardware, or firmware, and according to embodiments, a plurality of 'modules' or 'units' may be implemented as one element, it is also possible for one 'module' or 'part' to include a plurality of elements.

Hereinafter, the working principle and embodiments of present invention will be described with reference to the accompanying drawings.

In the present specification, an image may include a medical image obtained by a medical imaging apparatus such as a magnetic resonance imaging (MRI) device, a computed tomography (CT) device, an ultrasound imaging device, and an X-ray imaging device.

In the present specification, an "object" is to be photographed and may include a person, an animal, or a part thereof. For example, the object may include a part (organ) of a human body, a phantom, or the like.

Throughout the specification, an "ultrasonic image" means an image of the object, which is processed based on an ultrasonic signal transmitted to the object and reflected from the object.

In addition, throughout the specification, a 'user' may be a medical professional, such as a doctor, a nurse, a clinical pathologist, a medical imaging specialist, or a technician repairing a medical device, but is not limited thereto.

Hereinafter, the embodiments will be described in detail with reference to the accompanying drawings.

FIG. 1 is a block diagram illustrating a configuration of an ultrasonic diagnostic device 100 according to an embodiment. The ultrasonic diagnostic device 100 may include a probe 20, an ultrasonic transceiver 110, a controller 120, an image processing unit 130, a display unit 140, a storage unit 150, a communication unit 160, and an input unit 170.

The ultrasonic diagnostic device 100 may be implemented as a portable type as well as a cart type. Examples of a portable ultrasonic diagnostic device may include a smart phone, a laptop computer, a personal digital assistant (PDA), a tablet personal computer (PC), and the like including a probe and an application, but the present invention is not limited thereto.

The probe 20 may include a plurality of transducers. The plurality of transducers may transmit ultrasonic signals to an object 10 according to a transmission signal applied from a transmission unit 113. The plurality of transducers may receive ultrasonic signals reflected from the object 10 to form a reception signal. Further, the probe 20 may be implemented integrally with the ultrasonic diagnostic device 100 or may be implemented as a separate type in which the probe 20 is connected to the ultrasonic diagnostic device 100 in a wired or wireless manner. Further, the ultrasonic diagnostic device 100 may include one or more probes 20 according to an implementation form.

The controller 120 controls the transmission unit 113 to form a transmission signal to be applied to each of the plurality of transducers in consideration of the positions and focal points of the plurality of transducers included in the probe 20.

The controller 120 controls a reception unit 115 to convert a reception signal received from the probe 20 in an analog-to-digital conversion manner and to sum the digitally converted reception signal in consideration of the positions and focal points of the plurality of transducers, thereby generating ultrasonic data.

The image processing unit 130 generates an ultrasonic image using the ultrasonic data generated by the ultrasonic reception unit 115.

The display unit 140 may display the generated ultrasonic image and various pieces of information processed by the ultrasonic diagnostic device 100. The ultrasonic diagnostic device 100 may include one or more display units 140 according to an implementation form. Further, the display unit 140 may be implemented as a touch screen in combination with a touch panel.

The controller 120 may control the overall operation of the ultrasonic diagnostic device 100 and a signal flow between internal components of the ultrasonic diagnostic device 100. The controller 120 may include a memory that stores a program or data for performing a function of the ultrasonic diagnostic device 100 and a processor that processes the program or data. Further, the controller 120 may control the operation of the ultrasonic diagnosis device 100 by receiving a control signal from the input unit 170 or an external device.

The ultrasonic diagnostic device 100 may include the communication unit 160 and may be connected, through the communication unit 160, to an external device (for example, a server, a medical device, a portable device (a smart phone, a tablet PC, a wearable device, and the like)).

The communication unit 160 may include one or more components enabling communication with the external device and may include, for example, at least one of a short-range communication module, a wired communication module, and a wireless communication module.

The communication unit 160 may transmit and receive external devices and control signals and data.

The storage unit 150 may store various types of data or programs for driving and controlling the ultrasonic diagnostic device 100, input/output ultrasonic data, acquired ultrasonic images, and the like.

The input unit 170 may receive a user's input for controlling the ultrasonic diagnostic device 100. For example, user input includes buttons, keypad, mouse, trackball, jog switch, knob, etc., input, touch pad or touch screen, voice input, motion input, biometric information input (For example, iris recognition, fingerprint recognition, etc.) may be included, but the present invention is not limited thereto.

An example of the ultrasonic diagnostic device 100 according to an embodiment will be described later through FIGS. 2a to 2c.

Figure 2A:
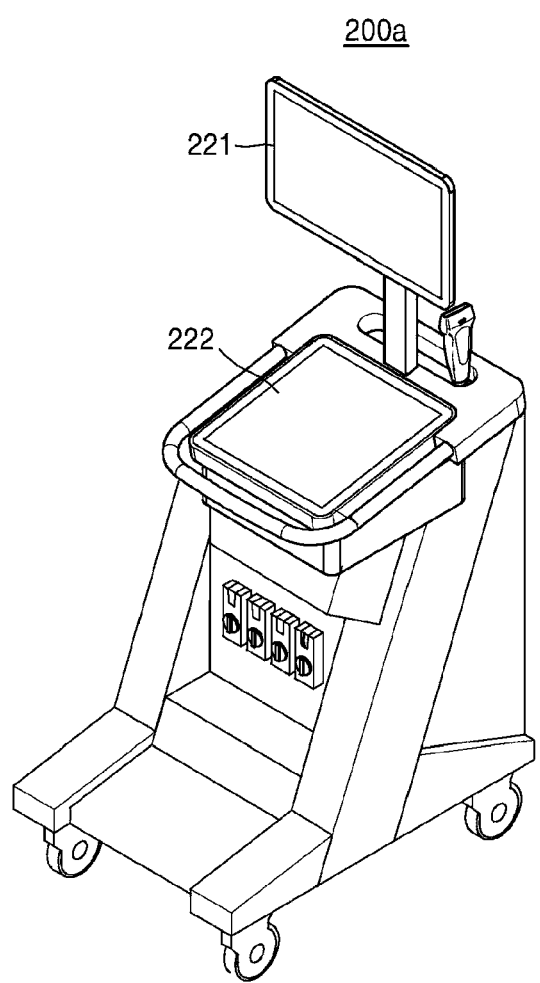
FIGS. 2a to 2c are views illustrating ultrasonic diagnostic device.
Figure 2B:
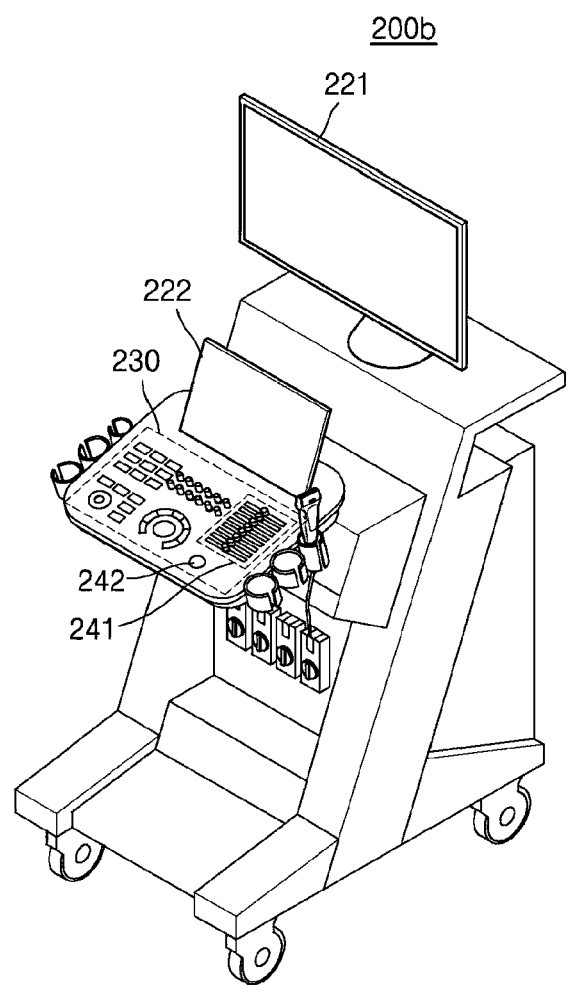
Figure 2C:
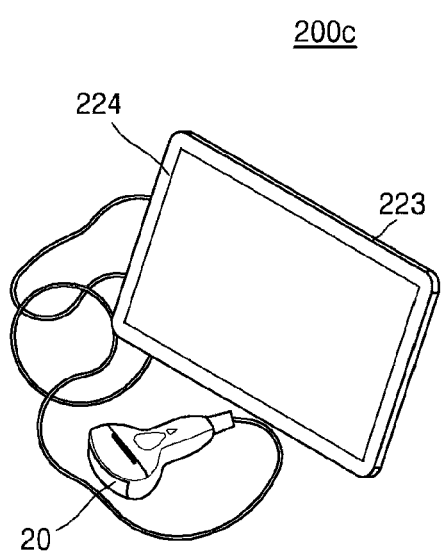

FIGS. 2a to 2c are views illustrating ultrasonic diagnostic devices according to an embodiment.

Referring to FIGS. 2a and 2b, ultrasonic diagnostic devices 200a and 200b may each include a main display unit 221 and a sub display unit 222. One of the main display unit 221 and the sub display unit 222 may be implemented as a touch screen. The main display unit 221 and the sub display unit 222 may display the ultrasonic image or various pieces of information processed by the ultrasonic diagnostic devices 200a and 100b. Further, the main display unit 221 and the sub display unit 222 may be implemented as a touch screen and provide a graphical user interface (GUI) to receive data for controlling the ultrasonic diagnostic devices 200a and 100b from a user. For example, the main display unit 221 may display the ultrasonic image, and the sub display unit 222 may display a control panel for controlling the ultrasonic image in the form of the GUI. The sub display unit 222 may receive data for controlling the displaying of the image through the control panel displayed in the form of the GUI. The ultrasonic diagnostic devices 200a and 100b may control, using input control data, the displaying of the ultrasonic image displayed on the main display unit 221.

Referring to FIG. 2b, the ultrasonic diagnostic device 100b may further include a control panel 230 in addition to the main display unit 221 and the sub display unit 222. The control panel 230 may include a button, a trackball, a jog switch, a knob, and the like, and may receive data for controlling the ultrasonic diagnostic device 100b from the user. For example, the control panel 230 may include a time gain compensation (TGC) button 241, a freeze button 242, and the like. The TGC button 241 is a button for setting a TGC value for each depth of the ultrasonic image. Further, when detecting the input of the freeze button 242 while scanning the ultrasonic image, the ultrasonic diagnostic device 100b may maintain a state in which a frame image at a corresponding time point is displayed.

Meanwhile, inputs of the button, the trackball, the jog switch, the knob, and the like included in the control panel 230 may be provided to the GUI in the main display unit 221 or the sub display unit 222.

Referring to FIG. 2c, the ultrasonic diagnostic device 100c may be implemented as a portable type. Examples of a portable ultrasonic diagnostic device 100c may include a smart phone, a laptop computer, a PDA, a tablet PC, and the like including a probe and an application, but the present invention is not limited thereto.

The ultrasonic diagnostic device 100c may include the probe 20 and a main body 223, and the probe 20 may be connected to one side of the main body 223 in a wired or wireless manner. The main body 223 may include a touch screen 224. The touch screen 224 may display the ultrasonic image, various pieces of information processed by the ultrasonic diagnostic device, the GUI, and the like.

Figure 3:
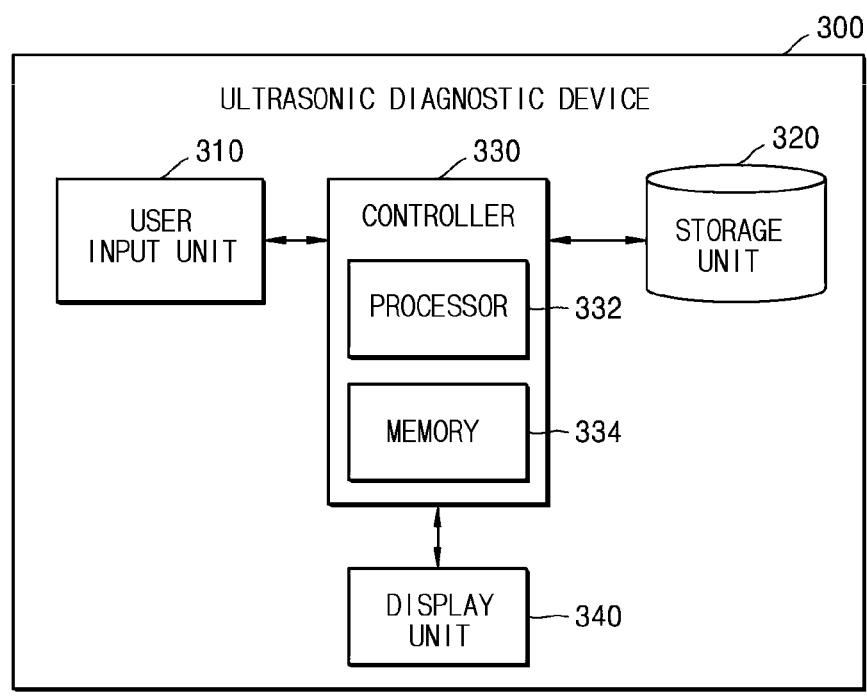
FIG. 3 is a block diagram illustrating components of an ultrasonic diagnostic device according to an embodiment of the present disclosure.

FIG. 3 is a block diagram illustrating components of an ultrasonic diagnostic device 300 according to an embodiment of the present disclosure. The ultrasonic diagnostic device 300 may be implemented as a cart-type as well as a portable-type. Examples of the portable-type ultrasonic diagnostic device may include a picture archiving and communications system (PACS) viewer, a smart phone, a laptop computer, a personal digital assistant (PDA), a tablet personal computer (PC), and the like, but the present disclosure is not limited thereto.

Referring to FIG. 3, the ultrasonic diagnostic device 300 may include a user input unit 310, a storage unit 320, a controller 330, and a display unit 340. FIG. 3 illustrates only essential components of the ultrasonic diagnostic device 300 according to an embodiment of the present disclosure, and the ultrasonic diagnostic device 300 may further include the probe 20, the ultrasonic transceiver 110, and the communication unit 160, which are illustrated in FIG. 1.

The user input unit 310 may receive an input of a user who manipulates the ultrasonic diagnostic device 300 while examining an object. The user input unit 310 may be configured as a control panel including hardware elements such as a key pad, a mouse, a trackball, a touch pad, and a jog switch, but the present disclosure is not limited thereto. In an embodiment, the user input unit 310 may be configured as a touch screen that receives a touch input and displays a graphical user interface (GUI).

The user input unit 310 may receive a user input for modifying set parameters while an ultrasound image of the object is captured by the ultrasonic diagnostic device 300. The user input unit 310 may receive a user input for modifying set parameters of a factory preset or may receive a user input for modifying set parameters of at least one user preset previously stored in the storage unit 320. In an embodiment, the user input unit 310 may receive a user input for storing a new user preset including the modified set parameters in a manner of overwriting an existing user preset with the new user preset. The user input unit 310 may also receive a user input for generating the new user preset including the modified set parameter.

In an embodiment, the user input unit 310 may receive a user input for setting a reference value related to a change history of the at least one user preset. In an embodiment, the user input unit 310 may receive a user input for setting a reference value related to a use history of the at least one user preset.

The storage unit 320 may include at least one of a volatile memory (e.g., a dynamic random-access memory (DRAM), a static RAM (SRAM), a synchronous DRAM (SDRAM), and the like), a non-volatile memory (e.g., a one time programmable read-only memory (OTPROM), a PROM, an erasable PROM (EPROM), an electrically erasable PROM (EEPROM), a mask ROM, a flash ROM, and the like), a hard disk drive (HDD), and a solid-state drive (SSD). In an embodiment, the storage unit 320 may also include a database.

The storage unit 320 may store the at least one user preset each including set parameter values used by the ultrasonic diagnostic device 300 to obtain an ultrasound image of an object. Here, the set parameters of the user preset may include at least one of, for example, time gain compensation (TGC), frequency, pulse repetition frequency (PRF), gain, depth, and ensemble. However, the set parameters are not limited to the above-listed examples. In an embodiment, the storage unit 320 may also store a factory setting, which is an initial set value, among set items of the ultrasonic diagnostic device 300.

The storage unit 320 may store set parameters, which are modified according to a user input received through the user input unit 310, as a user preset. In an embodiment, when the set parameters are modified by the user input, the storage unit 320 may store a change history of the user preset. In an embodiment, the storage unit 320 may store the change history of the at least one user preset in a log file format.

In an embodiment, the storage unit 320 may store use history information of each of the at least one user preset.

The controller 330 controls overall operations of the ultrasonic diagnostic device 300 and processes data and signals. The controller 330 may be configured as one or more hardware units. In an embodiment, the controller 330 may be configured as a hardware unit including a memory 344 that stores at least one of computer programs, instructions, algorithms, and application data, and a processor 342 that processes the programs, instructions, algorithms, or application data stored in the memory 344. The processor 342 may be configured as at least one of, for example, a central processing unit, a microprocessor, and a graphic processing unit. In this case, the processor 342 and the memory 344 may be configured as a single chip, but the present disclosure is not limited thereto. In another embodiment, the controller 330 may operate by one or more software modules that are generated by executing program codes stored in the memory 344.

The controller 330 may load the at least one user preset stored in the storage unit 320 and may modify the set parameters of the ultrasonic diagnostic device 300 according to a user input received through the user input unit 310. In an embodiment, the controller 330 may modify a parameter value of at least one of the TGC, the frequency, the PRF, the gain, the depth, and the ensemble based on the user input.

When the set parameter value of the at least one user preset is modified, the controller 330 may obtain change history information for the at least one user preset and store the change history information in the storage unit 320. In an embodiment, the controller 330 may obtain information about at least one of a period of modification of the set parameter, the number of modifications of the set parameter, the number of modified items of the set parameter, and modified variations of the set parameter value of each of the at least one user preset. In an embodiment, the controller 330 may store the obtained change history information of the at least one user preset in a log file format. The controller 330 may obtain use history information of the at least one user preset. In an embodiment, the controller 330 may obtain information about at least one of a period of use, a time of use, the number of uses, and the number of diagnosed patients of each of the at least one user preset. The controller 330 may store the obtained use history information in the storage unit 320 for each user preset. The controller 330 may obtain information about the history of using the at least one user preset for a specific time period from a time point at which an ultrasound image of the object is captured until a specific time point. Here, the specific time period may be set by a user input.

The controller 330 may display the change history information and the use history information of each of the at least one user preset on the display unit 340. In an embodiment, the controller 330 may display a value obtained by quantifying the change history information and the use history information for each of the at least one user preset in the form of a bar graph. However, the present disclosure is not limited thereto, and in another embodiment, the controller 330 may display the change history information and the use history information of the at least one user preset as letters, numerals, symbols, and the like.

The controller 330 may determine reliability of the at least one user preset based on the change history information and the use history information. Here, the reliability may refer to a degree to which the at least one user preset are optimized, and a highly reliable user preset may have a set parameter value capable of providing a high-quality ultrasound image. The controller 330 may determine the user preset having a set parameter with a low change history and a high use history as a highly reliable user preset. In an embodiment, as the period of modification of the set parameter increases, the number of modifications of the set parameter decreases, the number of modified items of the set parameter decreases, and the modified variations of the set parameter value decrease, the controller 330 may determine the user preset among the at least one user preset as a highly reliable user preset. In an embodiment, as a time of use, the number of uses, and the number of diagnosed patients during a preset time period increase, the controller 330 may determine the user preset among the at least one user preset as a highly reliable user preset.

The controller 330 may quantify the change history and the use history of the at least one user preset and display the quantified change history and use history on the display unit 340 in the form of a graph. In an embodiment, the controller 330 may display the user preset among the at least one user preset that has the change history whose quantified value is less than or equal to a preset first threshold and the use history whose quantified value is greater than or equal to a second preset threshold on the display unit 340.

The controller 330 may display a first user preset having high reliability among the at least one user preset stored in the storage unit 320 on the display unit 340. In an embodiment, the controller 330 may set a reference value related to the change history and the use history based on a user input received through the user input unit 310 and determine the user preset corresponding to the set reference value among the at least one user preset stored in the storage unit 320.

For example, the controller 330 may set a reference value related to at least one of the period of modification of the set parameter, the number of modifications of the set parameter, the number of modified items of the set parameter, and the modified variations of the set parameter value of the at least one user preset based on the user input, and the controller 330 may determine the user preset corresponding to the set reference value among the at least one user preset stored in the storage unit 320. The controller 330 may display the determined user preset on the display unit 340.

For example, the controller 330 may set a reference value related to at least one of the period of use, the time of use, the number of uses, and the number of diagnosed patients of each of the at least one user preset based on the received user input and determine the user preset corresponding to the set reference value among the at least one user preset previously stored in the storage unit 320. The controller 330 may display the determined user preset on the display unit 340.

In an embodiment, the controller 330 may set a diagnosis division to be diagnosed using a probe, which is selected based on the user input received through the user input unit 310, and display the user preset having high reliability among the user presets corresponding to the set diagnosis division on the display unit 340.

The display unit 340 may display a user interface (UI) related to items related to the set parameter value of the at least one user preset. For example, the display unit 340 may be configured as a physical device including at least one of a cathode ray tube (CRT) display, a liquid crystal display (LCD), a plasma display panel (PDP) display, an organic light-emitting display (OLED), a field emission display (FED), a light-emitting diode (LED) display, a vacuum fluorescent display (VFD), a digital light processing (DLP) display, a flat panel display (FPD), a three-dimensional (3D) display, and a transparent display, but the present disclosure is not limited thereto.

In an embodiment, the display unit 340 may be configured as a touch screen including a touch interface. When the display unit 340 is configured as a touch screen, the display unit 340 may be a component integrated with the user input unit 310 configured as a touch panel.

The display unit 340 may display a highly reliable user preset under the control of the controller 330. In an embodiment, the display unit 340 may display the quantified change history and use history of the at least one user preset in the form of a graph.

In an embodiment, the display unit 340 may include a main display unit, which displays an ultrasound image of an object, and a sub-display unit that displays a GUI of items related to the set parameter value of the at least one user preset.

Figure 4A:
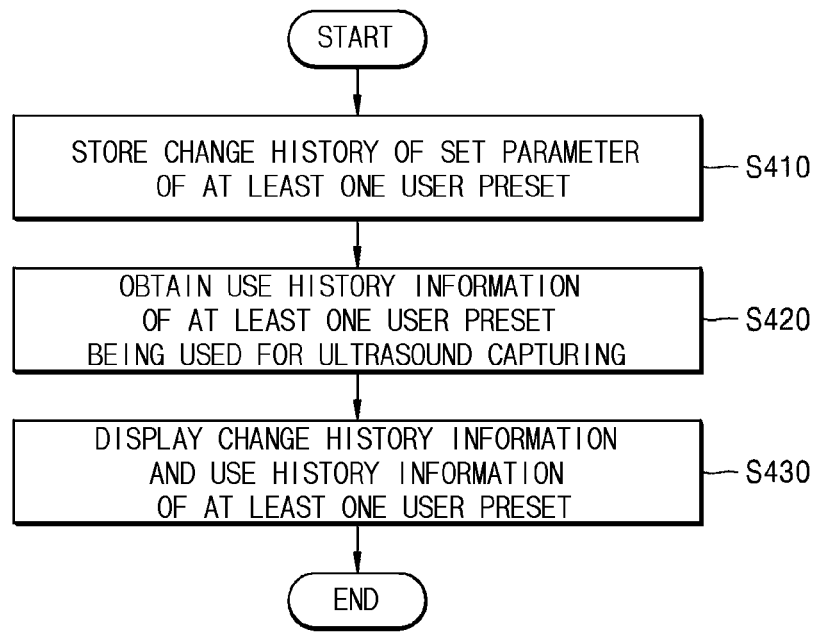
FIG. 4a is a flowchart illustrating a method of providing change history information and use history information of a user preset by the ultrasonic diagnostic device of the present disclosure.
Figure 4B:
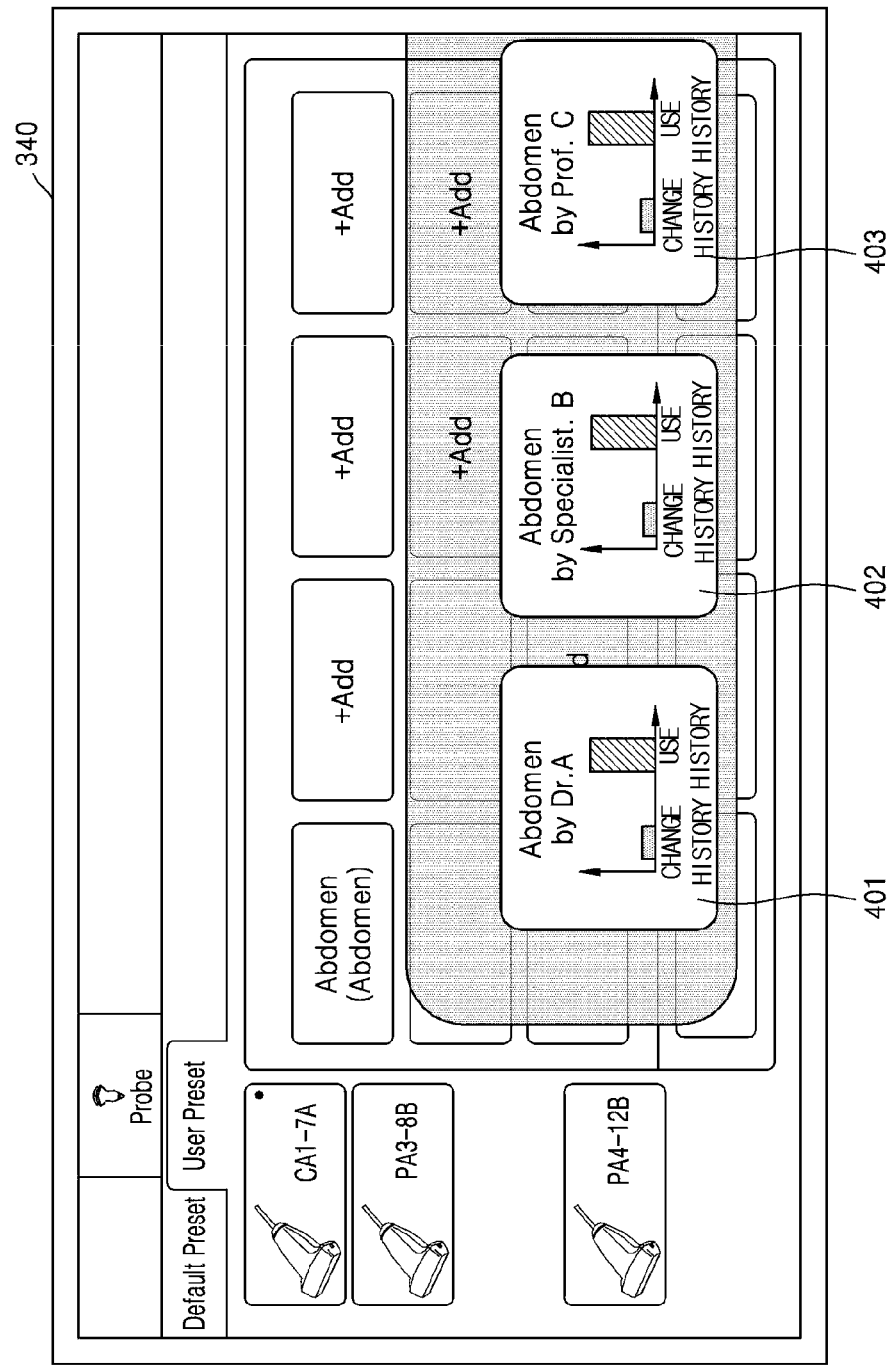
FIG. 4b is a diagram illustrating an embodiment in which the ultrasonic diagnostic device of the present disclosure displays the change history information and the use history information of the user preset.

FIG. 4a is a flowchart illustrating a method of providing change history information and use history information of a user preset by the ultrasonic diagnostic device of the present disclosure, and FIG. 4b is a diagram illustrating an embodiment in which the ultrasonic diagnostic device of the present disclosure displays the change history information and the use history information of the user preset.

In step S410 of FIG. 4a, the ultrasonic diagnostic device 300 stores a change history of a set parameter of at least one user preset. In an embodiment, the ultrasonic diagnostic device 300 may receive a user input for modifying a set parameter value of each of the previously stored at least one user preset. The ultrasonic diagnostic device 300 may store a change history of the at least one user preset, which is modified based on the user input, in a log file format. The change history may include at least one of a period of modification of the set parameter, the number of modifications of the set parameter, the number of modified items of the set parameter, and modified variations of the set parameter value of each of the at least one user preset.

In step S420, the ultrasonic diagnostic device 300 obtains use history information of the at least one user preset being used for ultrasound capturing. In an embodiment, the ultrasonic diagnostic device 300 may obtain information about at least one of a period of use, a time of use, the number of uses, and the number of diagnosed patients of each of the at least one user preset. In an embodiment, the ultrasonic diagnostic device 300 may obtain information about a history of using the at least one user preset during a time period from a time point at which an ultrasound image of the object is captured until a specific time point. Here, the specific time period may be set by a user input.

In step S430, the ultrasonic diagnostic device 300 displays the change history information and the use history information of the at least one user preset. Referring to FIG. 4B together, the display unit 340 of the ultrasonic diagnostic device 300 may display a value obtained by quantifying change history information and use history information of each of first to third user presets 401 to 403 in the form of a bar graph. However, the present disclosure is not limited thereto, and in another embodiment, the display unit 340 may display the change history information and the use history information of the first to third user presets 401, 402, and 403 as letters, numbers, symbols, and the like.

In an embodiment, the ultrasonic diagnostic device 300 may display identification information of a user that sets a parameter value of each of the at least one user preset. Referring to FIG. 4b together, the user that has modified a set parameter value of the first user preset 401 and has stored the modified value may be Dr. A. Similarly, identification information of the user that has stored a set parameter value of the second user preset 402 may be a specialist B, and identification information of the user that has stored a set parameter value of the third user preset 403 may be a professor C.

In an embodiment, the ultrasonic diagnostic device 300 may determine reliability of the at least one user preset based on the change history information and the use history information. The ultrasonic diagnostic device 300 may determine the user preset having a set parameter with a low change history and a high use history as a highly reliable user preset. In an embodiment, as a period of modification of the set parameter increases, the number of modifications of the set parameter decreases, the number of modified items of the set parameter decreases, and the modified variations of the set parameter value decrease, the ultrasonic diagnostic device 300 may determine the user preset among the at least one user preset as a highly reliable user preset. In an embodiment, as a time of use, the number of uses, and the number of diagnosed patients during a preset time period increase, the ultrasonic diagnostic device 300 may determine the user preset among the at least one user preset as a highly reliable user preset.

In an embodiment, the ultrasonic diagnostic device 300 may display the first user preset having high reliability among the previously stored at least one user preset. In an embodiment, the ultrasonic diagnostic device 300 may set a diagnosis division to be diagnosed using a probe, which is selected based on the received user input, and display the user preset having high reliability among the user presets corresponding to the set diagnosis division.

In general, when an object is examined using an ultrasonic diagnostic device, an initial value, that is, a factory preset, is not used, and set parameter values such as gain, depth, and TGC may be modified in a process of capturing an ultrasound image. The user preset is optimized in a manner of storing the modified set parameter values as a user preset, continuously modifying the set parameter values while a patient is captured, and overwriting the previously stored user preset with a new user preset. In order to optimize the user preset, a certain degree of time and effort is required. In addition, it takes a lot of time for a user, who does not have knowledge or is not experienced in an ultrasonic diagnostic device, to generate a preferred user preset. In addition, there is a problem in that, when the ultrasound image is captured using an unoptimized user preset, the quality of the obtained ultrasound image is not high, and thus it is difficult to obtain a highly reliable user preset.

The ultrasonic diagnostic device 300 according to the embodiment described with reference to FIGS. 3, 4a, and 4b may display a highly reliable user preset, i.e., the user preset that is optimized well based on the change history and the use history of each of the at least one user preset. Thus, the ultrasonic diagnostic device 300 of the present disclosure may reduce the time and effort required in the process of optimizing the user preset and, as a result, may improve user convenience. In addition, the ultrasonic diagnostic device 300 of the present disclosure may improve the quality of an ultrasound image by providing highly reliable user presets used by others.

Figure 5:
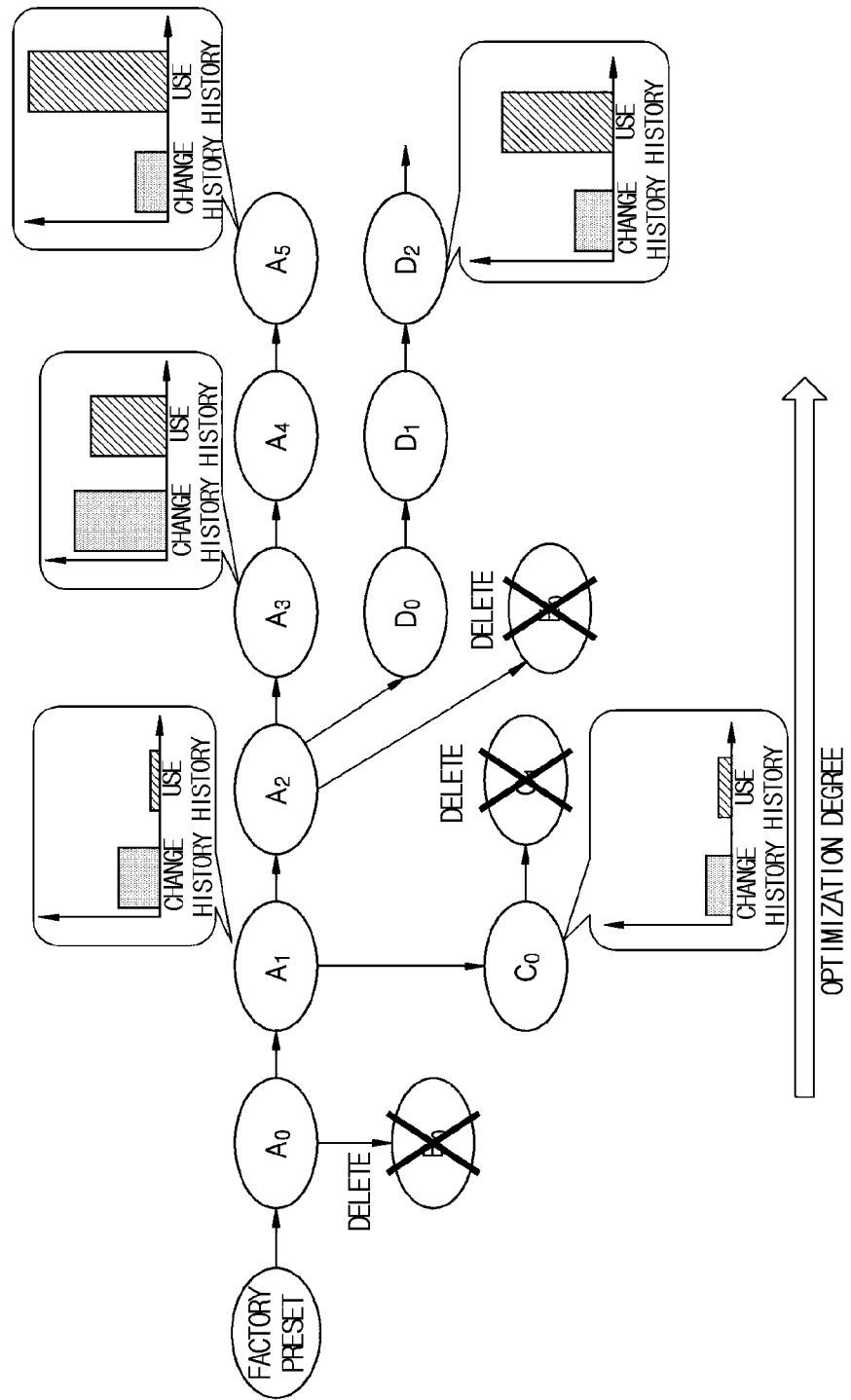
FIG. 5 is a diagram illustrating an embodiment in which the ultrasonic diagnostic device of the present disclosure optimizes a user preset.

FIG. 5 is a diagram illustrating an embodiment in which the ultrasonic diagnostic device 300 of the present disclosure optimizes a user preset.

Referring to FIG. 5, a degree of optimization of at least one user preset is illustrated. In FIG. 5, "A," "B," "C," "D," and "E" denote types of the user preset, and a numeral refers to an nth user preset newly updated by modifying a set parameter of the user preset and then storing the existing user preset in an overwrite manner by an nth user. For example, "$A_1$" may be a first user preset generated by modifying a set parameter of a user preset $A_0$, which is modified from a factory preset, and then storing the same again, and "$A_2$" may be a second user preset generated by modifying a set parameter of "$A_1$" and then storing the same again. A user preset $B_0$ may be a user preset generated by modifying the set parameter of "$A_0$," which is the previously stored user preset, and then storing the same with a new name. Similarly, "$C_0$" may be a user preset generated by modifying the set parameter of "$A_1$," which is the previously stored user preset, and then storing the same with a new name.

In the embodiment described with reference to FIG. 5, user presets $B_0$, $C_1$, and $E_0$ are deleted by the user.

Optimization degrees of user presets $A_0$ to $A_5$ may be different from each other. For example, in the case of the user preset $A_0$, a change history may be at an intermediate level while a use history, that is, a use frequency, may be at a low level. In the case of the user preset $A_3$, a change history may be at a high level, and a use frequency may also be at a high level. In the case of the user preset $A_5$, a change history may be at a low level while a use frequency may be at a high level. A level of each of a change history and a use frequency of the user preset $C_0$ may be similar to that of the user preset $A_1$. In addition, in the case of a user preset $D_2$, a change history may be at an intermediate level, but a use frequency may be at a high level.

Here, an optimized user preset refers to a user preset having a set parameter capable of obtaining a high-quality ultrasound image, and the optimization degree may refer to the reliability of the user preset. That is, the reliability of the user preset may become higher as the optimization degree is higher.

In an embodiment, the ultrasonic diagnostic device 300 may determine the user preset having a set parameter with a low change history and a high use history as a highly reliable user preset. For example, as a period of modification of the set parameter increases, the number of modifications of the set parameter decreases, the number of modified items of the set parameter decreases, and the modified variations of the set parameter value decrease, the ultrasonic diagnostic device 300 may determine the user preset as a highly reliable user preset. Further, as a time of use, the number of uses, and the number of diagnosed patients during a preset time period increase, the ultrasonic diagnostic device 300 may determine the user preset among the at least one user preset as a highly reliable user preset.

In the embodiment described with reference to FIG. 5, as a subscript numeral becomes higher, the user preset may be a highly optimized and reliable user preset. For example, the user preset $A_5$ has the change history with a low level and the use history, that is, a use frequency with a high level. This may mean that the user preset $A_5$ is in a state of completion of optimization and is a user preset that the user may trust, because even though the number of times and hours for the user to modify the set parameter of the user preset $A_5$, and the number of modified items in the set parameter are lower than those of other user presets, the user preset $A_5$ has the use frequency with a high level. Similarly, this may mean that the user preset $D_2$ is also the user preset in a state of completion of optimization because the change history is at a low level and the use frequency is at a high level. The relationship between the change history and the use history, and the optimization degree will be described with reference to FIGS. 6a and 6b.

Figure 6A:
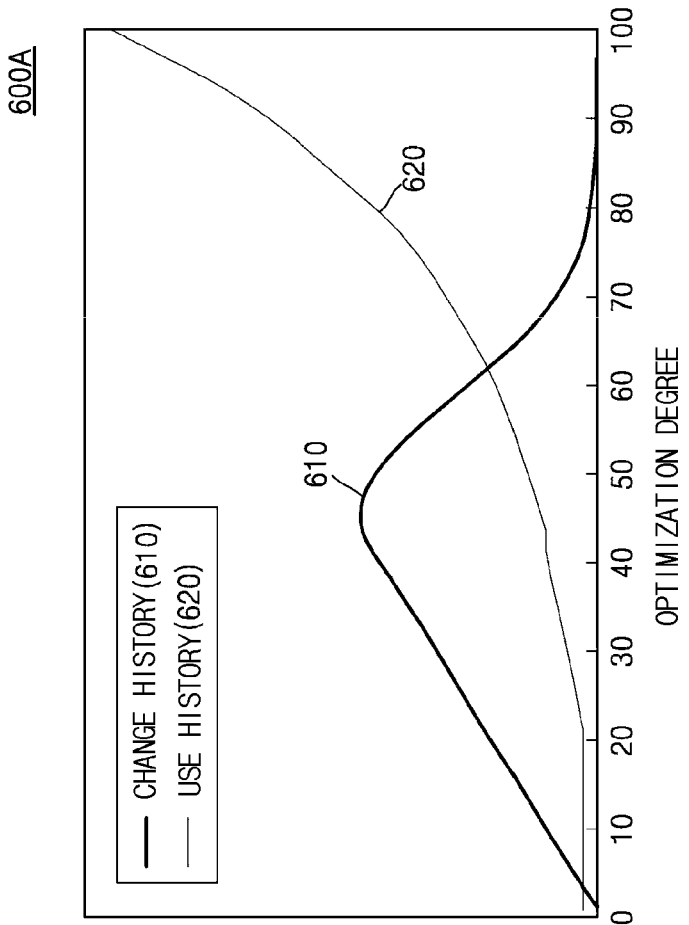
FIG. 6a is a graph illustrating an optimization degree according to a change history and a use history of a user preset.

FIG. 6a is a graph illustrating an optimization degree according to a change history 610 and a use history 620 of a user preset, and FIG. 6Bb is a table illustrating parameters representing the change history and the use history of the user preset.

Referring to FIG. 6a, graph 600A representing the optimization degree according to the change history 610 and the use history 620 of the user preset is illustrated. In graph 600A shown in FIG. 6a, the change history 610 may be a value obtained by quantifying at least one of, for example, the number of modifications of the set parameter, the number of modified items of the set parameter, and modification variations of a set parameter value in the user preset. The use history 620 may be a value obtained by quantifying at least one of, for example, a time of use, the number of uses, and the number of diagnosed patients of the user preset.

The change history 610 in graph 600A continues to rise until the optimization degree reaches 50%, but falls as the optimization degree exceeds 50%. That is, the change history 610 is saturated at a certain degree of value. That is, the set parameter of the user preset has a change history that rises in an initial stage of optimization and continues to rise up to an intermediate stage of optimization. This is because the set parameter is frequently modified in an ultrasound capturing step in order to obtain a high-quality ultrasound image, and the user preset is updated. The change history 610 falls as the optimization progresses to a completion stage after the intermediate stage. This is because the set parameter of the user preset is optimized to the extent that the set parameter is satisfied, and thus the number of modifications, the time of modification, the number of modified items, and the like of the set parameter are reduced.

Unlike the change history 610, the use history 620 continues to rise in proportion to the optimization degree. This is because the time of use, the number of uses, the number of diagnosed patients, and the like increase as the user preset becomes highly optimized.

Referring to table 600B shown in FIG. 6b, an example of a modification history, a use history, and an optimization degree of each of user presets A to D is illustrated. In table 600B, the change history may include information about a period of modification, the number of modified items, and the number of modifications, and the use history may include information about the number of uses, a period of use, a time of use, and the number of diagnosed patients. Numerals listed in table 600B are exemplary for convenience of description, and the change history and the use history of each of the user presets A to D are not limited to the numerals shown in table 600B.

Referring to the modification history, in the case of the user preset A, the period of modification is one year and two months ago, the number of modified items is 18, and the number of modifications is eight. In the case of the user preset B, the period of modification is one year and two months ago, the number of modified items is 17, and the number of modifications is nine. In the case of the user preset C, the period of modification is one day ago, the number of modified items is 182, and the number of modifications is 308. In the case of the user preset D, the period of modification is five days ago, the number of modified items is 162, and the number of modifications is 288. Referring to the modification history/use history graph, in the case of the user presets A and B, a value obtained by quantifying the change history is lower than that in the case of the user presets C and D. Here, the value obtained by quantifying the change history may be proportional to the number of modified items and the number of modifications and may become higher as the period of modification is more recent.

Referring to the use history, in the case of the user preset A, the number of uses is 4560, the period of use is one day ago, the time of use is 21562 minutes, and the number of diagnosed patients is 3402. In the case of the user preset B, the number of uses is 40, the period of use is one year and one month ago, the time of use is 262 minutes, and the number of diagnosed patients is 32. In the case of the user preset C, the number of uses is 45, the period of use is one day ago, the time of use is 302 minutes, and the number of diagnosed patients is 34. In the case of the user preset D, the number of uses is 4060, the period of use is one day ago, the time of use is 18562 minutes, and the number of diagnosed patients is 3002. Referring to the modification history/use history graph, in the case of the user presets A and D, a value obtained by quantifying the use history is lower than that in the case of the user presets B and C. Here, the quantified use history may be proportional to the number of uses, the time of use, and the number of diagnosed patients and may become higher as the period of use is more recent.

In table 600B, the optimization degree may be in a completion stage as the change history becomes lower and the use history becomes higher. For example, in the case of the user preset A in which the change history is at a low level and the use history is at a high level, the optimization may be in a completion stage. The user preset B is in an initial stage of optimization since both the change history and the use history are at a low level, and the user preset C may be in an initial stage of optimization since the change history is at a high level but the use history is at a low level. In addition, the user preset D may be in an intermediate stage of optimization since both the change history and the use history are at a high level.

In the embodiment described with reference to FIGS. 6a and 6b, as the change history 610 becomes lower and the use history 620 becomes higher, the optimization reaches a completion stage. This is because, in the user preset that allows high-quality ultrasound images to be obtained, the number of times the set parameter of the user preset is modified, the number of modified items in the set parameter, and the like decrease, and the number of uses, the time of use, and the number of diagnosed patients increase. That is, it may mean that the user preset is a highly reliable user preset as the user preset is further optimized. For example, the reliability of the user preset may become higher as the period of modification of the set parameter increases, the number of modifications decreases, the number of modified items of the set parameter decreases, and the modified variations of the set parameter value decrease. In addition, the reliability of the user preset may increase in proportion to the time of use of the user preset, the number of uses, and the number of diagnosed patients.

FIG. 7 is a diagram illustrating an example of a user interface for receiving a user input, which is used for setting reference values related to change history information and use history information of a user preset, by the ultrasonic diagnostic device of the present disclosure.

Referring to FIG. 7, the display unit 340 of the ultrasonic diagnostic device may display a user interface (UI) for receiving a user input for setting reference values related to change history information and use history information in order to provide a high-reliability user preset. The user interface may include a use history setting UI 710 for setting reference values for a use history of the user preset, and a change history UI 720 for setting reference values for a change history of the user preset.

The use history UI 710 may include a period-of-use setting UI 712, a time-of-use setting UI 714, a number-of-uses setting UI 716, and a number-of-diagnosed-patients setting UI 718. The period-of-use setting UI 712 may receive a user input for collecting information about the history of the user preset being used during a specific time period. The period-of-use setting UI 712 may receive a user input for setting an initial date and an end date used by the user preset. The ultrasonic diagnostic device may obtain information about the number of times used by the user preset, a time of use, and the number of diagnosed patients during the specified time period through the user input.

In an embodiment, based on the user input through the period-of-use setting UI 712, the ultrasonic diagnostic device may obtain information about the history of the user preset being used for capturing an object during a time period from a start time point (initial time) to a specific time point (end time) during which a user captures an ultrasound image of the object. The time period may be set in units of days, weeks, and years. In an embodiment, the ultrasonic diagnostic device may search for the user presets used during the time period between the start time point (initial time) to the specific time point (end time) set among at least one user preset previously stored in the storage unit 320 (see FIG. 3) and display the search results on the display unit 340 (see FIG. 3).

The time-of-use setting UI 714 may receive a user input for setting a reference value related to the user preset being used. The ultrasonic diagnostic device may set a reference value related to the time of use based on a user input received through the time-of-use setting UI 714 and determine the user preset corresponding to the set reference value among the previously stored at least one user preset. For example, when the user sets 100 days as the reference value, the ultrasonic diagnostic device may search for the user presets having the time of use of 100 days or more among the user presets previously stored in the storage unit 320 (see FIG. 3) and display the search results on the display unit 340 (see FIG. 3).

The number-of-uses setting UI 716 may receive a user input for setting a reference value related to the number of times for which the user preset has been used. The ultrasonic diagnostic device may set a reference value related to the number of uses based on a user input received through the number-of-uses setting UI 716 and determine the user preset corresponding to the set reference value among the previously stored at least one user preset. For example, when the user sets 100 times as the reference value, the ultrasonic diagnostic device may search for the user presets having the number of uses of 100 times or more among the user presets previously stored in the storage unit 320 (see FIG. 3) and display the search results on the display unit 340 (see FIG. 3).

The number-of-diagnosed-patients setting UI 718 may receive a user input for setting a reference value related to the number of patients diagnosed using the user preset. The ultrasonic diagnostic device may set a reference value related to the number of diagnosed patients based on a user input received through the number-of-diagnosed-patients setting UI 718 and determine the user preset corresponding to the set reference value among the previously stored at least one user preset. For example, when the user sets 10 patients as the reference value, the ultrasonic diagnostic device may search for the user presets having the number of diagnosed patients of 10 patients or more among the user presets previously stored in the storage unit 320 (see FIG. 3) and display the search results on the display unit 340 (see FIG. 3).

The change history setting UI 720 may include a period-of-modification setting UI 722, a number-of-modifications setting UI 724, a number-of-items-of-modified-parameters setting UI 726, and a modified-variations-of-parameter setting UI 728. The period-of-modification setting UI 722 may receive a user input for collecting information about the history of the user preset being modified during a specific time period. The period-of-use setting UI 712 may receive a user input for setting an initial date and an end date used by the user preset during which the set parameter value of the user preset has been modified. The ultrasonic diagnostic device may obtain information about the number of modifications of the user preset, the number of modified parameters, and modified variations of the parameter during the time period specified through the user input. The ultrasonic diagnostic device may search for the user presets having the change history during the specified time period among the at least one user preset previously stored in the storage unit 320 (see FIG. 3) and display the search results on the display unit 340 (see FIG. 3).

The number-of-modifications setting UI 724 may receive a user input for setting a reference value related to the number of modifications of the user preset. The ultrasonic diagnostic device may set a reference value related to the number of modifications based on a user input received through the number-of-modifications setting UI 724 and determine the user preset corresponding to the set reference value among the previously stored at least one user preset. For example, when the user sets 100 times as the reference value, the ultrasonic diagnostic device may search for the user presets, whose set parameters have been modified more than 100 times, among the user presets previously stored in the storage unit 320 (see FIG. 3) and display the search results on the display unit 340 (see FIG. 3).

The number-of-items-of-modified-parameters setting UI 726 may receive a user input for setting a reference value related to the number of modified items of the set parameter among the set parameters of the user preset. The ultrasonic diagnostic device may set a reference value related to the number of modified items of the set parameter based on a user input received through the number-of-items-of-modified-parameters setting UI 726 and determine the user preset corresponding to the set reference value among the previously stored at least one user preset. For example, when the user sets five as the reference value, the ultrasonic diagnostic device may search for the user presets in which more than five set parameters have been modified among the user presets previously stored in the storage unit 320 (see FIG. 3) and display the search results on the display unit 340 (see FIG. 3).

The modified-variations-of-parameter setting UI 728 may receive a user input for setting a reference value related to the degree of modification of the set parameter value of the user preset. The ultrasonic diagnostic device may set a reference value related to the modified variations of the set parameter value based on a user input received through the modified-variations-of-parameter setting UI 728 and determine the user preset corresponding to the set reference value among the previously stored at least one user preset. For example, when the user sets a gain value to 10, the ultrasonic diagnostic device may search for the user presets having a gain value of 10 or more among the user presets previously stored in the storage unit 320 (see FIG. 3) and display the search results on the display unit 340 (see FIG. 3).

In the ultrasonic diagnostic device of the present disclosure, through the UI shown in FIG. 7, a reference value may be set, and user presets that match criteria desired by a user are automatically searched and provided so that user convenience may be improved. Further, the ultrasonic diagnostic device of the present disclosure may provide only user presets corresponding to the reference value set by the user so that reliability may be improved.

Figure 8:
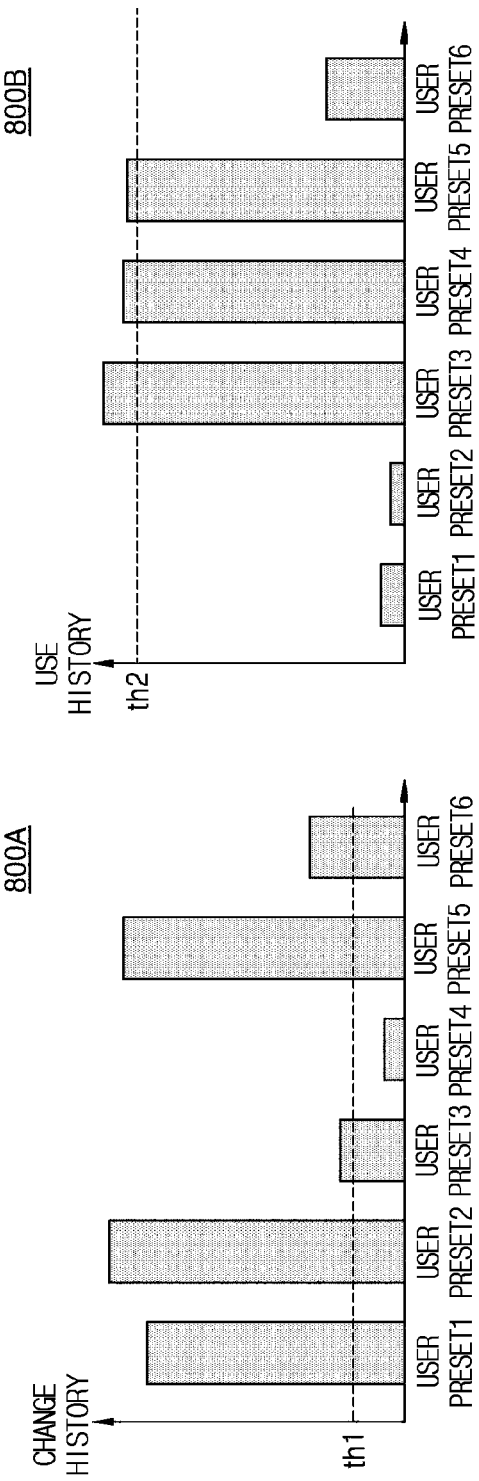
FIG. 8 is a diagram illustrating an embodiment in which a highly reliable user preset is determined based on a change history and a use history by the ultrasonic diagnostic device of the present disclosure.

FIG. 8 is a diagram illustrating an embodiment in which a highly reliable user preset is determined based on a change history and a use history by the ultrasonic diagnostic device of the present disclosure.

Referring to FIG. 8, change history graph 800A obtained by quantifying change history information of user presets 1 to 6 and use history graph 800B obtained by quantifying use history information of the user presets 1 to 6 are illustrated.

Referring to change history graph 800A, quantified modification histories of the user presets 1 to 6 are shown in the form of a bar graph. The change history shown in the change history graph 800A may be a value obtained by quantifying at least one of a period of modification of a set parameter, the number of modifications of the set parameter, the number of modified items of the set parameter, and modified variations of the set parameter value of each of the user presets 1 to 6. The change history may be proportional to the number of modified items of the set parameter, the number of modifications, and the modified variations of the set parameter value. In an embodiment, the change history may be quantified with a higher value as the period of modification is more recent.

The ultrasonic diagnostic device may determine the user preset having a quantified change history of less than or equal to a first threshold th1 as a highly reliable user preset. In the embodiment described with reference to FIG. 8, the ultrasonic diagnostic device may determine the user preset 4 having a change history of less than or equal to the first threshold th1 as a highly reliable user preset.

Referring to use history graph 800B, quantified use histories of the user presets 1 to 6 are shown in the form of a bar graph. The use history shown in use history graph 800B may be a value obtained by quantifying at least one of a period of use, a time of use, the number of uses, and the number of diagnosed patients of each of the user presets 1 to 6. The use history may be proportional to the time of use, the number of uses, and the number of diagnosed patients. In an embodiment, the use history may be quantified with a higher value as the period of use is more recent.

The ultrasonic diagnostic device may determine the user preset having a quantified use history of greater than or equal to a second threshold th2 as a highly reliable user preset. In the embodiment described with reference to FIG. 8, the ultrasonic diagnostic device may determine the user presets 3, 4, and 5 having a use history of greater than or equal to the second threshold th2 as a highly reliable user preset.

In an embodiment, the ultrasonic diagnostic device may determine the user preset that has a change history of less than or equal to the first threshold th1 and a use history of greater than or equal to the second threshold th2 as a highly reliable user preset. In the embodiment described with reference to FIG. 8, the ultrasonic diagnostic device may determine the user preset 4 as a highly reliable user preset. In an embodiment, the ultrasonic diagnostic device may display the user preset 4 determined as a highly reliable user preset on the display unit 340 (see FIG. 3).

Figure 9:
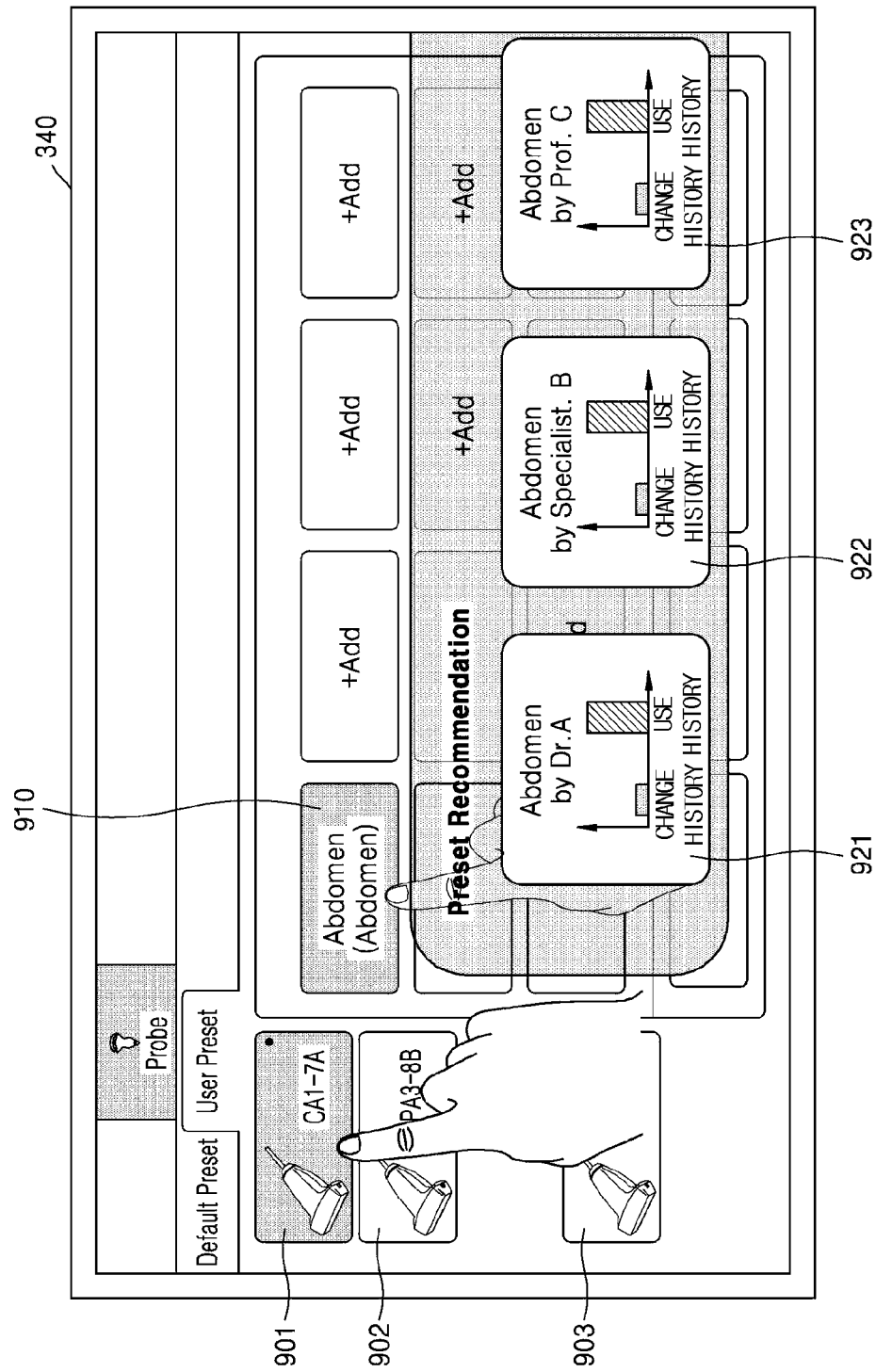
FIG. 9 is a diagram illustrating an embodiment in which a highly reliable user preset is provided based on a probe, which is selected by a user input, by the ultrasonic diagnostic device of the present disclosure.

FIG. 9 is a diagram illustrating an embodiment in which a highly reliable user preset is provided based on a probe, which is selected by a user input, by the ultrasonic diagnostic device of the present disclosure.

Referring to FIG. 9, the display unit 340 of the ultrasonic diagnostic device may display a UI for receiving a user input for selecting a probe and a UI for providing a highly reliable user preset among user presets corresponding to a diagnosis division that may be diagnosed using the selected probe.

In an embodiment, the display unit 340 may display a thumbnail image related to each of first to third probes 901 to 903. The ultrasonic diagnostic device may receive a user input for selecting a specific probe through the thumbnail image related to each of the first to third probes 901 to 903 in order to capture an ultrasound image of an object. In the embodiment described with reference to FIG. 9, the ultrasonic diagnostic device may receive a user input for selecting the first probe 901 labeled as CA1-7A.

The ultrasonic diagnostic device may set a diagnosis division, which may be examined using the selected first probe 901, based on the received user input. For example, when the first probe 901 is a probe used for diagnosis of abdomen, the ultrasonic diagnostic device may display a UI, through which a user input for selecting an abdominal diagnosis 910 is received, when the first probe 901 is selected. In an embodiment, the ultrasonic diagnostic device may set the abdominal diagnosis 910 as the diagnosis division based on the user input. However, the present disclosure is not limited thereto, and when the first probe 901 is selected, the ultrasonic diagnostic device may automatically set the abdominal diagnosis 910 as the diagnosis division.

The ultrasonic diagnostic device may display a UI that provides a user with a highly reliable user preset among the user presets corresponding to the set diagnosis division. In an embodiment, the ultrasonic diagnostic device may select at least one user preset corresponding to the abdominal diagnosis 910 among the user presets previously stored in the storage unit 320 (see FIG. 3) and display the user preset with a low change history and a high use history among the selected at least one user preset. In the embodiment described with reference to FIG. 9, the ultrasonic diagnostic device may display first to third user presets 921 to 923 on the display unit 340.

In an embodiment, the display unit 340 may display identification information of a user who has set parameter values of each of the first to third user presets 921 to 923. In an embodiment, the display unit 340 may display a graph obtained by quantifying a change history and a use history of each of the first to third user presets 921 to 923.

Figure 10:
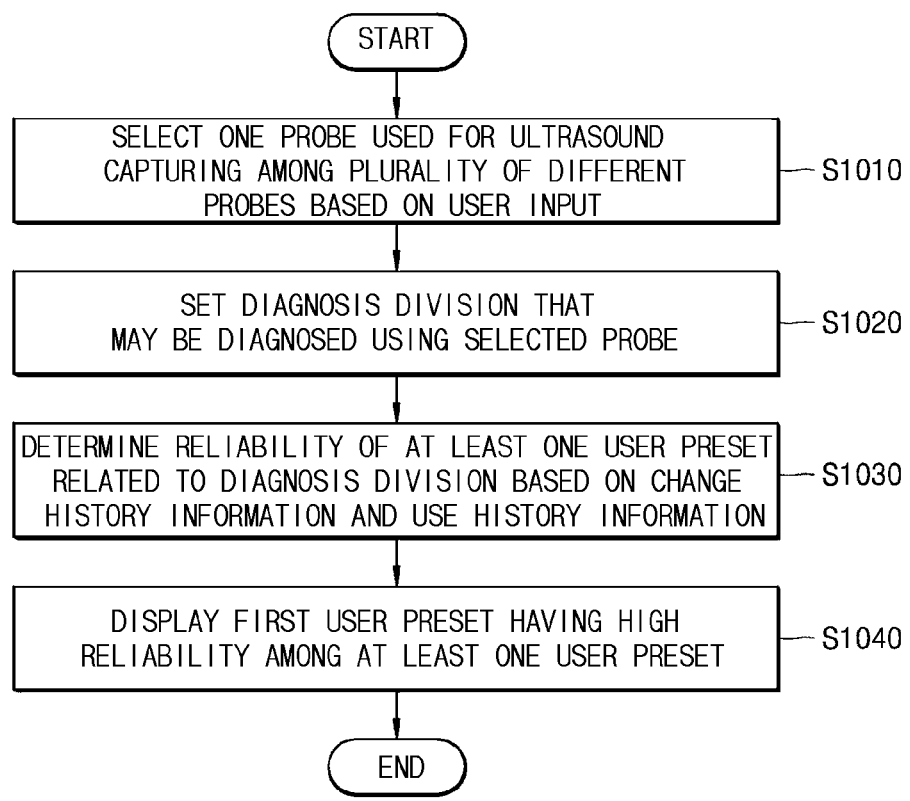
FIG. 10 is a flowchart illustrating a method of providing a highly reliable user preset based on a probe, which is selected by a user input, by the ultrasonic diagnostic device of the present disclosure.

FIG. 10 is a flowchart illustrating a method of providing a highly reliable user preset based on a probe, which is selected by a user input, by the ultrasonic diagnostic device of the present disclosure.

In step S1010, the ultrasonic diagnostic device selects one probe used for ultrasound capturing among a plurality of different probes based on a user input. In an embodiment, the ultrasonic diagnostic device may display a UI that includes a thumbnail image and identification information of each of the plurality of probes. The ultrasonic diagnostic device may receive a user input for selecting a probe through the UI displayed on the display unit and select the probe to be used for ultrasound capturing based on the user input.

In step S1020, the ultrasonic diagnostic device may set a diagnosis division that may be diagnosed using the selected probe. In an embodiment, the ultrasonic diagnostic device may display a UI that includes a list or thumbnail image related to the diagnosis division that may be diagnosed using the selected probe. The ultrasonic diagnostic device may select the diagnosis division based on the user input received through the displayed UI. In another embodiment, the ultrasonic diagnostic device may automatically set the diagnosis division that may be diagnosed using the selected probe.

In step S1030, the ultrasonic diagnostic device determines the reliability of at least one user preset related to the diagnosis division based on change history information and use history information. In an embodiment, the ultrasonic diagnostic device may select at least one user preset corresponding to the set diagnosis division from the at least one user preset previously stored in the storage unit 320 (see FIG. 3) and determine the reliability of the selected at least one user preset. The ultrasonic diagnostic device may determine the user preset with a low change history and a high use history as a highly reliable user preset.

In step S1040, the ultrasonic diagnostic device displays a first user preset having high reliability among the at least one user preset. In an embodiment, the ultrasonic diagnostic device may display the first user preset with a low change history and a high use history on the display unit 340 (see FIG. 3) among the at least one user preset corresponding to the diagnosis division that is set in step S1020.

In the embodiment described with reference to FIGS. 9 and 10, the ultrasonic diagnostic device may recommend a reliable user preset in a diagnosis division that may be diagnosed using a probe selected by a user, thereby improving user convenience. In addition, the ultrasonic diagnostic device of the present disclosure may provide an option of selecting the user preset based on the reputation of other users by displaying identification information of key opinion leaders such as well-known doctors, professors, and radiologists who have set parameter values of the recommended user preset. In addition, the ultrasonic diagnostic device of the present disclosure may improve intuition in selecting the user preset by displaying a value obtained by quantifying a change history and a use history of the recommended user preset in the form of a bar graph.

Figure 11:
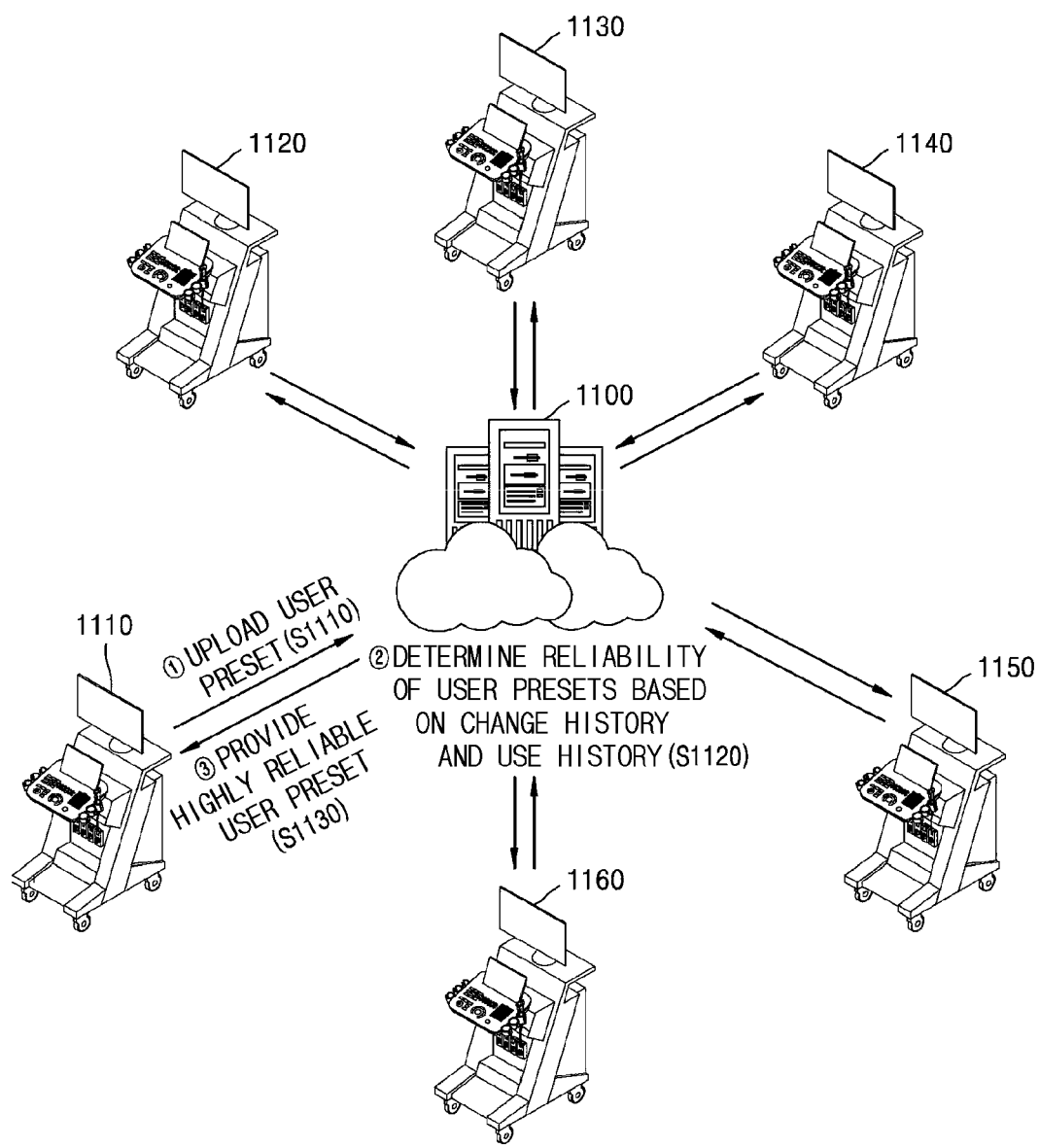
FIG. 11 is a diagram illustrating an embodiment in which each of ultrasonic diagnostic devices of the present disclosure uploads a user preset to a cloud server and receives a highly reliable user preset from the cloud server.

FIG. 11 is a diagram illustrating an embodiment in which each of ultrasonic diagnostic devices of the present disclosure uploads a user preset to a cloud server and receives a highly reliable user preset from the cloud server.

Referring to FIG. 11, a plurality of ultrasonic diagnostic devices 1110 to 1160 may be connected to a cloud server 1100 through a wired or wireless communication network. The plurality of ultrasonic diagnostic devices 1110 to 1160 may be ultrasonic diagnostic devices in one hospital, but the present disclosure is not limited thereto. In an embodiment, each of the plurality of ultrasonic diagnostic devices 1110 to 1160 may be ultrasonic diagnostic devices used in other hospitals.

In an embodiment, all the plurality of ultrasonic diagnostic devices 1110 to 1160 may be apparatuses of the same manufacturer or the same type and may have the same specification. However, the present disclosure is not limited thereto.

The plurality of ultrasonic diagnostic devices 1110 to 1160 may each upload a user preset including parameter values set by a user to the cloud server 1100. In step S1110, a first ultrasonic diagnostic device 1100 may upload the user preset, which is set by the user or stored in an overwrite manner after modifying a set parameter to the cloud server 1100. Here, the first ultrasonic diagnostic device 1100 may upload a log file including a change history and a use history of the user preset to the cloud server 1100. The change history of the user preset uploaded to the cloud server 1100 may be information, for example, about at least one of a period of modification of the set parameter, the number of modifications, the number of modified items of the set parameter, and modified variations of the set parameter value of the user preset. In addition, the use history of the user preset uploaded to the cloud server 1100 may be, for example, information about at least one of a period of use, a time of use, the number of uses, and the number of diagnosed patients of the user preset.

In step S1120, the cloud server 1100 may store a plurality of user presets received from the plurality of ultrasonic diagnostic devices 1110 to 1160 in a Big Data form and determine the reliability of each of the plurality of user presets based on the change history and the use history of each of the plurality of stored user presets. In an embodiment, as the period of modification of the set parameter of the plurality of user presets increases, the number of modifications of the set parameter decrease, the number of modified items of the set parameter of the plurality of user presets decreases, and the modified variations of the set parameter value decrease, the cloud server 1100 may determine the user preset is highly reliable. In an embodiment, the cloud server 1100 may determine the reliability of the user preset in proportion to the time of use, the number of uses, and the number of diagnosed patients of each of the plurality of user presets.

In step S1130, the first ultrasonic diagnostic device 1110 receives a highly reliable user preset from the cloud server 1100. The first ultrasonic diagnostic device 1110 may receive the highly reliable user preset from the cloud server 1100 through the wired or wireless communication network. In an embodiment, the first ultrasonic diagnostic device 1110 may receive identification information of a creator of the received user preset together with information about a diagnosis division.

In the embodiment described with reference to FIG. 11, the plurality of ultrasonic diagnostic devices 1110 to 1160 may each upload the user preset set by each user to the cloud server 1100, and the cloud server 1100 may manage the uploaded plurality of user presets in the form of Big Data, and thus the user presets may be shared between the plurality of ultrasonic diagnostic devices 1110 to 1160 in the same hospital or the plurality of ultrasonic diagnostic devices 1110 to 1160 in a plurality of other hospitals. Accordingly, one embodiment of the present disclosure allows user presets used by well-known doctors or professors to be used in other hospitals or other ultrasonic diagnostic devices.

The embodiments of the disclosure may be implemented as a software program including instructions stored in computer-readable storage media.

A computer may refer to a device capable of retrieving instructions stored in the storage media and performing operations according to embodiments of the disclosure in response to the retrieved instructions and may include X-ray systems according to the embodiments of the disclosure.

The computer-readable storage media may be provided in the form of non-transitory storage media. Here, the term "non-transitory" only means that the storage media do not include signals and are tangible, and the term does not distinguish between data that is semi-permanently stored and data that is temporarily stored in the storage media.

In addition, the ultrasonic diagnostic device and the method of operating the same according to the disclosed embodiments may be included in a computer program product. The computer program product may be traded, as a commodity, between a seller and a buyer.

The computer program product may include a software program and a computer-readable storage medium having the software program stored thereon. For example, the computer program product may include a product (e.g., a downloadable application) in the form of a software program electronically distributed by a manufacturer of an ultrasonic diagnostic device or through an electronic market (e.g., Google Play Store, and App Store). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a device (e.g., an ultrasonic diagnostic device), the computer program product may include a storage medium of the server or a storage medium of the device. Alternatively, in a case in which a third device (e.g., a smart phone) is communicationally connected to the server or device, the computer program product may include a storage medium of the third device. Alternatively, the computer program product may include a software program that is transmitted from the server to the device or the third device or that is transmitted from the third device to a terminal.

In this case, one of the server, the device, and the third device may execute the computer program product to perform the method according to the disclosed embodiments. Alternatively, two or more of the server, the device, and the third device may execute the computer program product to perform the method according to the disclosed embodiments in a distributed manner.

For example, the server (e.g., a cloud server, an artificial intelligence (AI) server, or the like) may run the computer program product stored therein to control the device communicationally connected to the server to perform the method according to the disclosed embodiments.

As another example, the third device may execute the computer program product to control the device communicationally connected to the third device to perform the method according to the disclosed embodiments When the third device executes the computer program product, the third device may download the computer program product from the server and execute the downloaded computer program product. Alternatively, the third device may execute the computer program product provided in a pre-loaded state to perform the method according to the disclosed embodiments.

Meanwhile, the embodiments may be implemented in the form of a recording medium storing instructions executable by a computer. The instruction may be stored in the form of a program code, and when executed by a processor, a program module may be generated to perform the operation of the disclosed embodiments. The recording medium may be implemented as a computer-readable recording medium.

As described above, the disclosed embodiments have been described with reference to the accompanying drawings. Those of ordinary skill in the art to which the present invention pertains will understand that the present invention may be practiced in a form different from the disclosed embodiments without changing the technical spirit or essential features of the present invention. The disclosed embodiments are illustrative and should not be construed as limiting.

The invention claimed is:

1. An ultrasonic diagnostic device providing a user preset, the ultrasonic diagnostic device comprising:
   a display unit;
   a storage unit storing at least one user preset;
   a user input unit configured to receive a user input for changing a set parameter of the at least one user preset; and
   a controller configured to:
      store, in the storage unit, change history information of the at least one user preset, whose the set parameter is changed based on the user input, wherein the change history information includes information about at least one of a period of modification of the set parameter, a number of modified items of the set parameter, and modified variations of the set parameter value of each of the at least one user preset, obtain use history information that is used by the at least one user preset in capturing an ultrasound image of an object, store the obtained use history information in the storage unit, determine reliability of the at least one user preset based on at least one of the period of modification of the set parameter, the number of modified items of the set parameter, and the modified variations of the set parameter value, and control the display unit to display a first user preset having highest reliability from among the at least one user preset, wherein the reliability is determined to be proportional to the period of modification of the set parameter and inversely proportional to the number of modified items of the set parameter and the modified variations of the set parameter value.

2. The ultrasonic diagnostic device of claim 1, wherein the user input unit is further configured to receive a user input for setting a reference value related to the at least one of the period of modification of the set parameter, the number of items of the set parameter, and the modified variations of the set parameter value, and the controller is further configured to set the reference value related to the at least one of the period of modification of the set parameter, the number of items of the set parameter, and the modified variations of the set parameter value based on the received user input and determine user preset corresponding to the set reference value among the at least one user preset.

3. The ultrasonic diagnostic device of claim 1, wherein the use history information includes information about at least one of a period of use, a time of use, a number of uses, and a number of diagnosed patients of each of the at least one user preset, the user input unit is further configured to receive a user input for setting a reference value related to at least one of the period of use, the time of use, the number of uses, and the number of diagnosed patients of each of the at least one user preset, and the controller is further configured to set the reference value related to at least one of the period of use, the time of use, the number of uses, and the number of diagnosed patients of each of the at least one user preset based on the received user input and determine the user preset corresponding to the set reference value among the at least one user preset.

4. The ultrasonic diagnostic device of claim 1, wherein the controller is further configured to:
quantify the change history information and the use history information of the at least one user preset, and
control the display unit to display the quantified change history information and the use history information on the display unit in the form of a graph.

5. The ultrasonic diagnostic device of claim 1, wherein the user input unit is further configured to receive a user input for selecting one probe, which is used for capturing the object, among a plurality of different probes, and the controller is further configured to:
set a diagnosis division that is diagnosed using the selected probe based on the received user input, and
control the display unit to display a second user preset having high reliability among the at least one user preset corresponding to the set diagnosis division.

6. A method of providing a user preset by an ultrasonic diagnostic device, the method comprising steps of:
storing change history information of at least one user preset when a set parameter of the at least one user preset is modified, wherein the change history information includes information about at least one of a period of modification of the set parameter, a number of modified items of the set parameter, and modified variations of the set parameter value of each of the at least one user preset;

obtaining use history information used by the at least one user preset in capturing an ultrasound image of an object and storing the obtained use history information;

determining reliability of the at least one user preset based on at least one of the period of modification of the set parameter, the number of modified items of the set parameter, and the modified variations of the set parameter value; and displaying a first user preset having highest reliability from among the at least one user preset, wherein the reliability is determined to be proportional to the period of modification of the set parameter and inversely proportional to the number of modified items of the set parameter and the modified variations of the set parameter value.

7. The method of claim 6, further comprising:
setting, based on a user input received by a user input unit, a reference value related to at least one of the period of modification of the set parameter, the number of modified items of the set parameter, and the modified variations of the set parameter value .

8. The method of claim 6, wherein,
the use history information includes information about at least one of a period of use, a time of use, a number of uses, and a number of diagnosed patients of each of the at least one user preset, and
a reference value related to at least one of the period of use, the time of use, the number of uses, and the number of diagnosed patients of each of the at least one user preset is set based on a user input.

9. The method of claim 6, wherein in the step of determining the reliability of the at least one user preset, the reliability of the at least one user preset is determined in proportion to a time of use, a number of uses, and a number of diagnosed patients of the at least one user preset during a preset time period.

10. The method of claim 6, further comprising steps of:
selecting one probe, which is used for capturing the object, among a plurality of different probes based on a user input; and
setting a diagnosis division that is diagnosed using the selected probe,
wherein in the step of displaying the at least one user preset, a second user preset having high reliability is displayed among the user presets corresponding to the set diagnosis division.

11. A non-transitory computer-readable recording medium in which a program for executing the method of claim 6 on a computer is recorded.

* * * * *